United States Patent
Ruocco et al.

(10) Patent No.: US 7,256,700 B1
(45) Date of Patent: Aug. 14, 2007

(54) IGNITION INTERLOCK DEVICE AND METHOD

(75) Inventors: John T. Ruocco, Mastic, NY (US); Ronald A. Koppel, Ronkonkoma, NY (US)

(73) Assignee: Interceptor Ignition Interlocks Inc., Pawling, NY (US)

( * ) Notice: Subject to any disclaimer, the term of this patent is extended or adjusted under 35 U.S.C. 154(b) by 83 days.

(21) Appl. No.: 10/987,507

(22) Filed: Nov. 12, 2004

Related U.S. Application Data

(60) Provisional application No. 60/519,219, filed on Nov. 12, 2003.

(51) Int. Cl.
*G08B 23/00* (2006.01)
(52) U.S. Cl. .................. 340/576; 340/339.12; 340/438
(58) Field of Classification Search ................ 340/576, 340/438, 339.12
See application file for complete search history.

(56) References Cited

U.S. PATENT DOCUMENTS

| | | | | |
|---|---|---|---|---|
| 4,096,161 A | * | 6/1978 | Shinohara et al. .......... | 556/467 |
| 4,158,198 A | * | 6/1979 | Ochiai ........................ | 340/576 |
| 4,185,198 A | * | 1/1980 | Fujimoto .................... | 378/98.5 |
| 4,689,603 A | * | 8/1987 | Conigliaro et al. ........ | 307/10.4 |
| 4,738,333 A | * | 4/1988 | Collier et al. ............... | 180/272 |
| 4,901,058 A | * | 2/1990 | Comeau et al. ............. | 340/576 |
| 4,902,628 A | * | 2/1990 | Blair .......................... | 436/132 |
| 5,224,566 A | * | 7/1993 | Stepanian et al. .......... | 180/272 |
| 6,748,792 B1 | * | 6/2004 | Freund et al. ............... | 73/23.3 |
| 6,853,956 B2 | * | 2/2005 | Ballard et al. .............. | 702/183 |
| 6,956,484 B2 | * | 10/2005 | Crespo ........................ | 340/576 |
| 2003/0183437 A1 | * | 10/2003 | Mendoza .................... | 180/272 |
| 2004/0083031 A1 | * | 4/2004 | Okezie .......................... | 701/1 |

\* cited by examiner

*Primary Examiner*—Jeffery Hofsass
*Assistant Examiner*—Edny Labbees
(74) *Attorney, Agent, or Firm*—Schweitzer Cornman Gross & Bondell LLP

(57) ABSTRACT

An apparatus for monitoring the alcohol content of an individual, preferably in connection with vehicle operation, has a sensor head coupled to a remote control module. The sensor head measures both breath pressure and breath alcohol levels. The data from the sensor head is processed by the control module to determine whether a valid breath sample exists and what action is to be taken based upon the alcohol level of the breath.

5 Claims, 4 Drawing Sheets

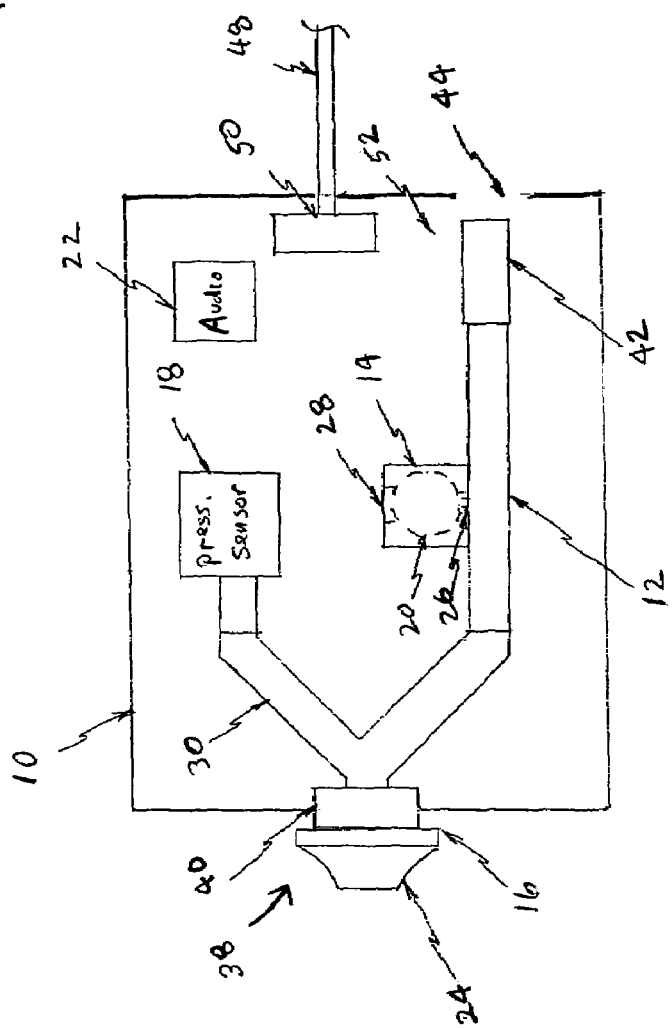
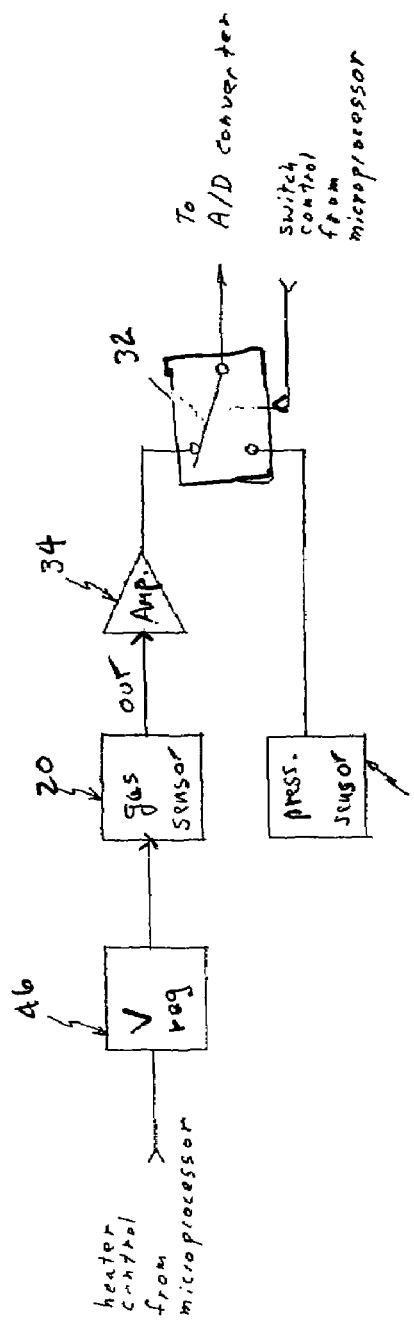

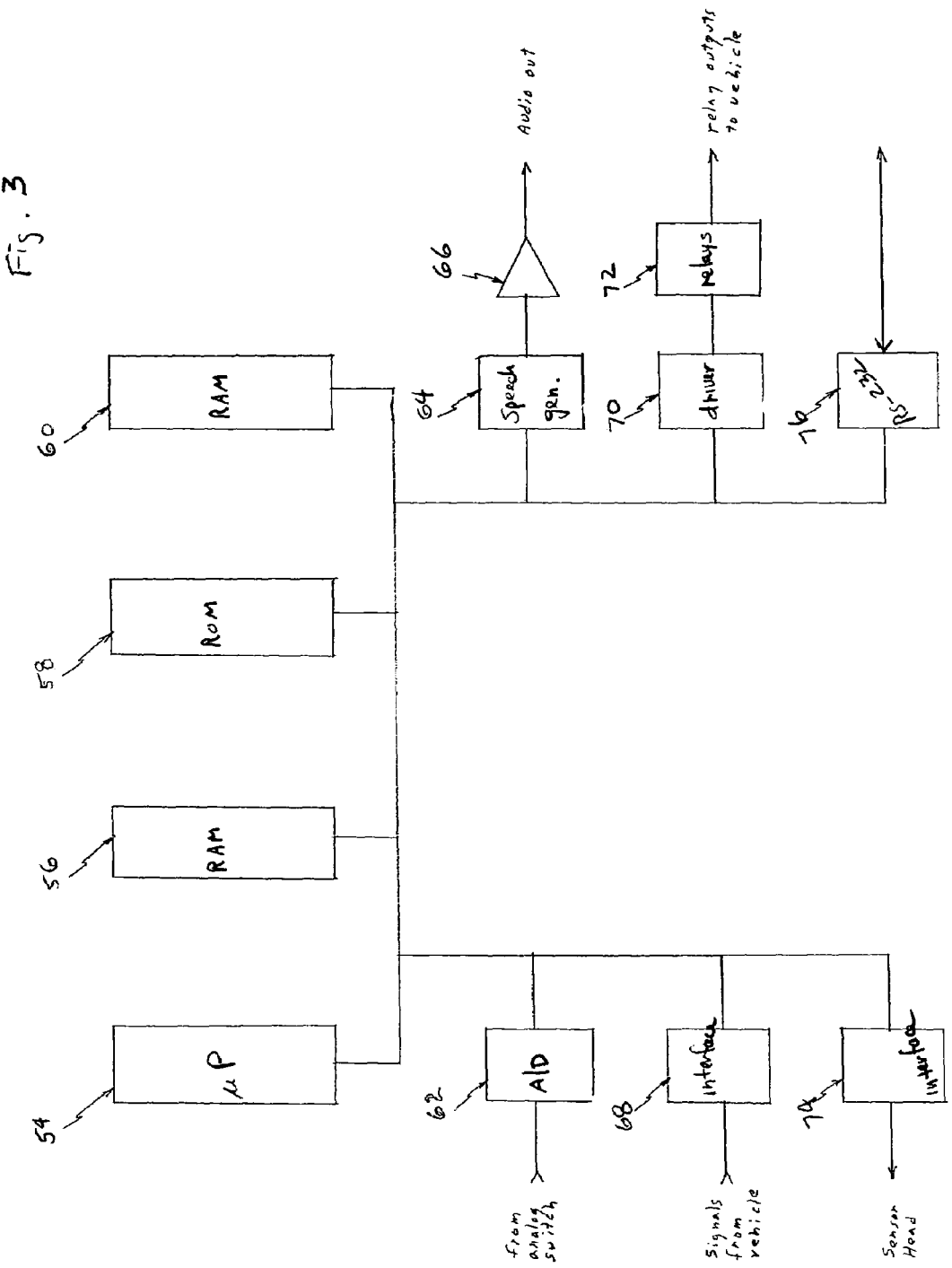

IGNITION INTERLOCK DEVICE AND METHOD

The present invention relates to a vehicle ignition interlock device, and in particular to such a device that is responsive to an input signal, such as a signal derived from a measurement of an individual's breath alcohol level, to serve as a deterrent from operating a vehicle when in an alcohol-impaired state. The present application claims the benefit of Provisional Patent Application No. 60/519,219 of Nov. 12, 2003.

BACKGROUND OF THE INVENTION

It is well recognized that the consumption of alcoholic beverages resulting in intoxication constitutes a significant public health and safety risk. Blood alcohol level is a well-recognized determinant for establishing liability under "driving while intoxicated" and "driving while impaired" statutes. It is also well appreciated that the degree of alcohol in the breath is an accurate determinant of blood alcohol level. Thus, there have been numerous devices developed to sense and measure breath alcohol levels, and particularly to serve as an analyzer or testing system in conjunction with an automotive ignition system interlock. Depending upon the breath alcohol level recorded, the vehicle may be prevented from starting, prevented from further operating, or caused to emit a warning or alarm.

It is accordingly the purpose of the present invention to provide an ignition interlock device which is responsive to the alcohol level in a sensed breath sample which is of broad applicability, which provides an audible interface with the user/driver, and which is of accurate operation.

BRIEF DESCRIPTION OF THE INVENTION

In accordance with the foregoing and other objects and features, an ignition interlock device constructed in accordance with the present invention comprises a sensor head assembly and a control module. The sensor head includes a breath passageway and a gas sensor for generating an electrical output representative to the level of breath alcohol. The control module receives the electrical signal from the sensor head and contains a microprocessor and associated memory. The device uses audible indicators and messaging to communicate with the driver, allowing the driver to concentrate on the road without having to look at displays, and may include voice synthesis circuitry to provide voice messages during operation. The control module also includes inputs for other sensors whereby the system's operation may be coordinated with and subject to other inputs which relate to various vehicle operating parameters.

BRIEF DESCRIPTION OF THE DRAWINGS

FIG. 1 is a diagram of the sensor head of the invention;

FIG. 2 is a block diagram of the circuitry of the sensor head;

FIG. 3 is a block diagram of the control module;

DETAILED DESCRIPTION OF THE INVENTION

Figure 4:
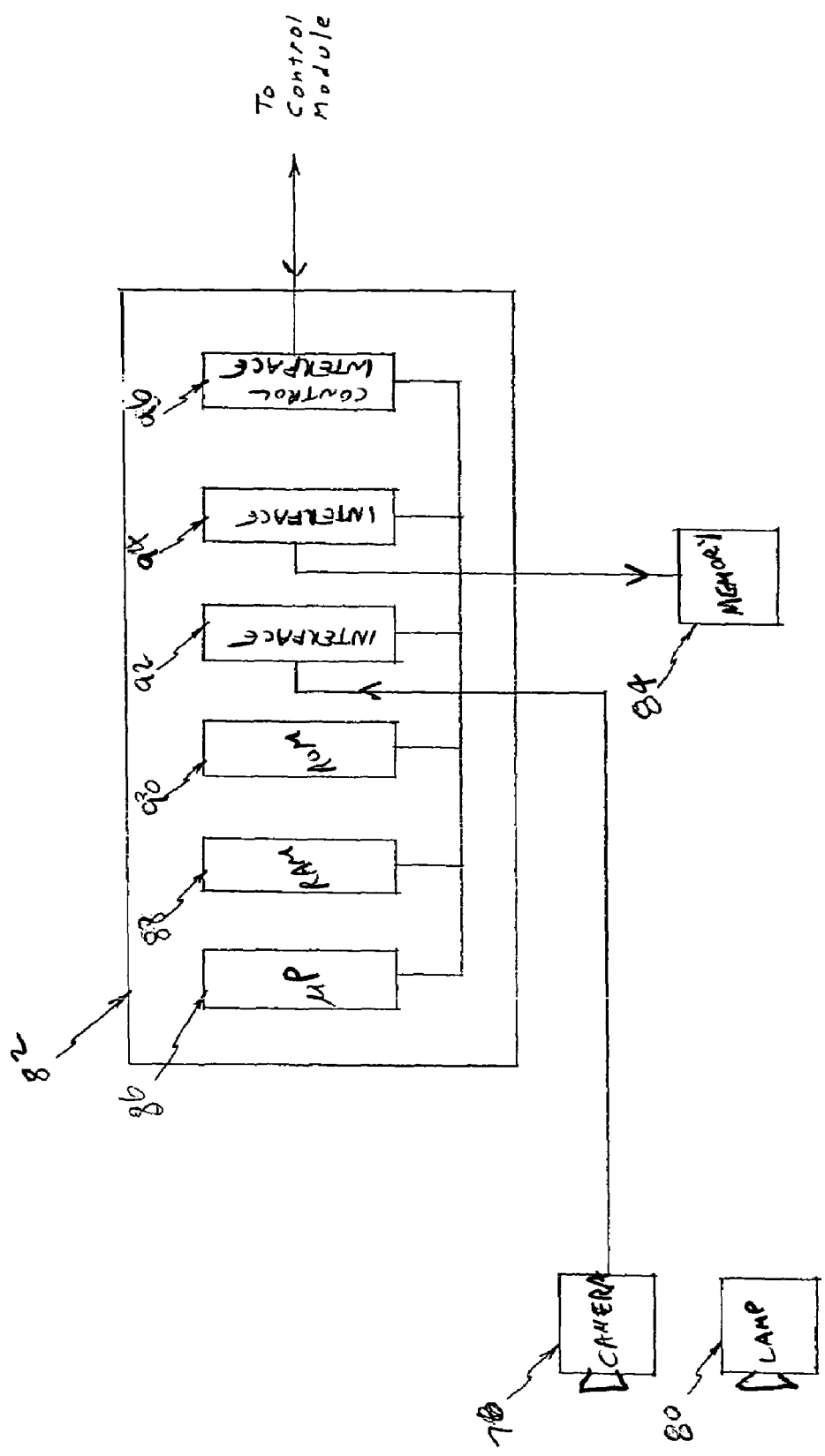
FIG. 4 is a block diagram of an enhancement to the invention to provide photographic records.

The present invention relates to an ignition interlock device for cars, commercial vehicles and other vehicles such as (but not limited to) motorcycles, airplanes, boats, trains, etc., and to an ignition interlock device that is intended to prevent an intoxicated driver from operating such a motor vehicle. The device is comprised of two parts, a sensor head assembly and a control module, which are interconnected by a cable.

The sensor head 10 is depicted in FIG. 1. The sensor head in the form of a housing having six main components: an air sample tube 12; an air chamber 14; a moisture and spit trap 16; a pressure sensor 18; a gas sensor 20; and an audible transducer 22. The air sample tube 12 may be approximately 2" long with a 0.15" inside diameter. A small orifice (0.02" in diameter) 26 is located in the side of the air sample tube, approximately midway along its length, and connects the tube to the air chamber 14, allowing a portion of a breath sample in tube to enter the air chamber. The air chamber is designed to be self-evacuating. An exhaust port 28 having a cross-sectional area several times larger than that of the inlet orifice is located on the side of the air chamber opposite the orifice 26, provides pressure equalization, and allows evacuation of the air chamber without developing significant backpressure in the air chamber. The exhaust port may be approximately 0.15"×0.075". Gas sensor 20, responsive to ethanol, is located in the air chamber. It may sit on a floor of the chamber, with a top sensing surface positioned just below the inlet orifice such that the incoming breath sample is directed over the sensing surface. Any one of a variety of sensors known in the art, such as the TGS line of Figaro USA, Inc. of Glenview, Ill., or sensors by FiS of Japan, distributed by Advanced Sensor Products of Canada or sensors by FiS of Japan, distributed by Advanced Sensor Products of Canada, may be employed. The FiS SB31 is particularly preferred. As known, the resistance of the sensor is a function of the concentration of the gas to which it is responsive. The air chamber is made large enough to accommodate the gas sensor (approximately 0.3" in diameter). However, the chamber space above the sensor may be limited to provide a small volume that allows the air chamber contents to be exchanged several times during a breath sample. This may be accomplished by incorporating a small ridge around a portion of an inside circumference of the air chamber which comes in contact with the top of the sensor, creating a baffle-like barrier and regulating the size of the space.

The air sample tube 12 is connected to the moisture/spit trap 16 through one end of a Y-tube 30, which joins the sample tube 12 to the sensor head mouthpiece 24. The pressure sensor 18, such as an 0-1.5 psi gauge, Motorola MPX5010GP, is connected to the other leg of the Y-tube. When a breath sample is provided a back pressure is created in the air sample tube. This pressure causes part of the sample to enter the air chamber 14 through the inlet orifice 26 due to the pressure differential resulting from the initially lower pressure in the air chamber. As previously indicated, the air chamber is limited in volume to allow its contents to be replaced several times during a breath sample. This prevents dilution of a current breath sample by residual air present in the air chamber.

The breath pressure is also applied to the pressure sensor 18 through the Y-tube. This allows both the pressure and duration of the breath sample to be measured by monitoring sensor output. Since the volume of air going through the air sample tube is related to the pressure and the duration of the flow, the total volume of air exhaled can be determined. This ensures that a deep lung breath sample, which is important for an accurate alcohol concentration measurement, has been provided.

As depicted in FIG. 2, the outputs of both pressure sensor 18 and gas sensor 20 are coupled through electronic analog switch 32 to an A/D converter in the control unit by a shielded wire. The position of the switch is controlled by the microprocessor in the control unit. The output of the gas sensor is buffered by amplifier 34.

The sensor head 10 also contains audible transducer 22, which can be an electronic buzzer, used to provide information to the user/driver without requiring the driver to look at a display, allowing the driver to concentrate on the road. In a preferred embodiment, the audible transducer provides a first indication, such as a continuous tone, during a breath sample input so long as the breath sample is of the correct pressure and is continuing towards the proper duration. This provides feedback to the user, allowing the user to continue providing the sample. Once a breath sample of the correct pressure is received for the specified duration the transducer provides a second indication, such as two short duration tones, indicating to the user that the breath sample is valid. A similar indication can be generated prior to the start of a breath sample to indicate that the system is ready to accept a breath sample. All indications are under microprocessor control. Other components and circuitry that may be required to drive the transducer and sensors, and buffer or condition their outputs, are conventional in nature and are not shown.

Preferably, the system defines and recognizes upper and lower limits for the breath sample pressure. These limits are changed midway through the breath sample. The limit change can be indicated to the user by another indication, such as three short tones with a shorter duration than the initial two tones. The user is required to blow with a moderate pressure during the first interval of the breath sample, and then with a stronger pressure during the second interval of the breath sample. The pressure readings from pressure sensor 18 are compared to values stored in non-volatile RAM located in the control unit for both intervals of the breath sample. An acceptance window, bounded by the upper and lower limits pressure values, allows rejection of pressure readings that are either too high or too low. This "two blow" method prevents mechanically-generated air samples from being accepted as valid breath samples, as it is difficult to provide and regulate such an air source, particularly in the context of the driver's seat of an automobile or other vehicle. Attempted circumvention attempts, such as by use of a balloon to generate an airflow, are thus minimized, while still providing ease of use for an individual. Such an approach can be contrasted with other systems that require a hum tone, for example, or other input forms that can be awkward to provide. With a tube construction having the foregoing dimensions, sensed pressure levels of 0.16 psi and 0.41 psi, respectively, have been found to provide suitable results. The durations for each breath interval may be on the order of 3 seconds.

The air sample tube is used in conjunction with the spit trap 16 to remove water from the breath air stream. This allows for a simple spit trap design that is washable and reusable. The spit trap, located at the central entrance arm of the Y-tube, adjacent the mouthpiece, may consist of a fine mesh screen that prevents excess moisture from entering the air sample tube and eventually the air chamber. The spit trap may be made part of a mouthpiece assembly 38. The mouthpiece assembly is preferably designed so that it is to be used with the mouthpiece portion touching only the outside of the user's lips. This reduces the quantity of moisture accumulation that can occur with other designs that require the user to put a tube in his or her mouth. The mouthpiece assembly is attached to the Y-tube through header assembly 40, allowing the mouthpiece to be easily removed for washing and to allow interchange of personalized mouthpieces. The Y-tube can be formed as an integral part of the header assembly to reduce production costs.

The small diameter of orifice 26 in the air sample tube further reduces the amount of moisture entering air chamber 14. The distal end of the air sample tube 12 is provided with flexible tube 42, the open end of which is positioned adjacent vent aperture 44 in the sensor head. The momentum of remaining moisture is the air stream tends to be carried past the orifice 26, and is carried by the continuing air stream in the sample tube through flexible tube 42 and out through vent aperture 44, allowing the moisture in the air sample tube to be vented to the outside atmosphere and preventing condensation in the sensor head. As shown, the end of the tube 42 may be kept a small distance from the vent aperture hole to prevent the user's hand from blocking the air flow, whereby in such situations the tube 42 can still vent into the interior of the sensor head. The tube 42 is flexible so that it can be bent to conform to the inner construction of the sensor head, allowing the vent aperture 44 to be located as desired and appropriate.

The gas sensor 20 itself is operated and controlled in a manner so as to reduce the amount of time before a test result is generated. Typically, sensors such as the Figaro line of sensors include an integral heating element, and require a stabilization/oxidation interval before an accurate gas level reading can be obtained. The present invention provides for overlap between the required stabilization/oxidation and the breath sample interval. That is, sensor output is allowed to continue stabilizing during the initial portion of a breath sample, in contrast to waiting for the output to completely stabilize prior to receipt of a breath sample. If the breath sample has no alcohol present, the sensor output will continue to decrease during the breath sample interval. However, if there is alcohol present the sensor output will stop decreasing and remain constant or start increasing, depending on the alcohol concentration. By the end of the sample period stabilization will have occurred; allowing a reading to be obtained in a relatively short amount of time, improving the ease of use of the device.

As set forth above, sensor 20 includes a heater that raises the temperature of the active sensor element, typically a metal oxide, to a certain temperature to generate a space change layer from adsorbed oxygen, and the stabilization period is associated with this heating. As shown in FIG. 2, the heater in the sensor is controlled by voltage regulator 46, which in turn is controlled by the microprocessor and is kept off to conserve power until just prior to a request for a breath sample. The heater is then turned on by the microprocessor and a small delay period is initiated. This allows the sensor the opportunity to start to stabilize (referred to as "initial action"). This delay is small, and is typically 5 to 10 seconds. The request for a breath sample is then provided. The heater remains on during sample reception and continues to heat and stabilize as the breath sample is started. At the end of the breath sample the heater remains energized through a small following delay period which allows the sensor enough time to fully react the received sample but is short enough that the concentration of the sample in the air chamber remains unchanged (as the user has stopped providing a breath)

subject to leakage through the exhaust port 28. This delay may be approximately 5 to 8 seconds. After this delay the heater is turned off and the sensing period terminated. As may be recognized, any sensor used should have a relatively small sensing element to provide a fast response time to allow this type of operation.

During the interval when the breath sample is being provided, the pressure sensor 18 is selected and activated by analog switch 32 and its output signal fed to the microprocessor in the control unit. When the microprocessor determines that the end of a proper breath sample has been received, with a correct pressure contour and duration as described above, an output signal from the pressure sensor is no longer required. The switch 32 selects the output from the gas sensor 20 and is delivered to the control unit. The selective switching reduces the number of shielded wires required to couple the sensor head to the control unit. The wires may be part of a sensor head cable 48 depicted in FIG. 1, connected to the sensor head by a connector 50 mounted on a circuit board 52 upon which sensor head components are mounted within the head 10.

The control unit or module is depicted in FIG. 3, and contains a microprocessor 54, such as a Texas Instruments TM5320OC203PZ with conventional storage RAM 56; ROM 58 and nonvolatile RAM 60 for storage of event and setup data. A/D converter 62, such as a Texas Instruments TLC1550IFN, converts analog signals passed by the sensor head analog switch 32 to digital form for processing by the microprocessor. Speech processor/generator 64, such as an ISD model 2575S also under microprocessor control, generates speech commands and instructions; its output is fed to audio amplifier 66. A multiple line interface 68 is provided for receipt of signals from the vehicle; while relay driver/interface 70, driving multiple relay outputs 72, allows switched control of vehicle systems. Sensor head interface 74 provides necessary control and operation signals to the sensor head. An RS-232 interface 76 is also provided.

The relay outputs 72 can control vehicle systems, such as the vehicle's lights and/or horn, to provide a variety of functions, including a visual or audible warning in the event a rolling retest, which is a breath test given after the vehicle engine has been started, is failed; control of the vehicle's starter motor to prevent the vehicle from being started if the driver's breath alcohol level is over the breath alcohol limit set point; and muting of the vehicle's radio (among other devices) during generated voice messages or sensor head control signal issuance. The output of audio amplifier 66 may be fed to an external speaker (not shown), but can alternatively be connected to the vehicle's speaker system using a set of relay outputs 72 to switch between the vehicle's radio/audio system output and the audio amplifier.

The microprocessor and control module also control the operation of the sensor head components as described above through interface 74 to control the analog switch 32, the gas sensor 20's heater, and audio transducer 22. The output of the analog switch 32 is directed to A/D converter 62 through a shielded wire in the sensor head cable. The sensor head cable may be connected to a mating cable from the control module through a small quick-disconnect inline connector. Such a construction allows the sensor head to be easily removed from the vehicle, providing a vehicle anti-theft feature, particularly if a relay output 72 is connected to the vehicle's starter circuit as described above, since the interlock device will not allow the engine to be started without a proper output from the sensor head.

The control module, through the microprocessor, further controls all aspects of the system's operation, including providing instructions to the driver through voice messages. The methodology is conventional in nature. The messages allow the driver to concentrate on the road rather than watching a display. The messages may include, but are not limited to, reporting the result of a breath test, providing a warning to stop the vehicle if a rolling retest has been failed, providing information whether the vehicle may be started, and generating an alert message to the driver several seconds prior to the request for a breath sample. An optional parental keyswitch can be attached to vehicle input interface 68 to allow an authorized individual, such as a parent of a child for whom the unit was purchased, to override the system.

All features of the control module are programmable through the RS-232 interface 76, which may have two levels of programming access. A first level is intended for the installation for the system and may include, but need not be limited to, a selection of the language for voice messages, and entry of the current date and time. A second, higher level of programming is intended for the factory and may include, but need not be limited to, establishment of setpoints for the initial breath test and subsequent rolling retests; limits for the breath pressure and duration; the scheduling and duration of rolling retests; the intended use of the system, such as voluntary, mandate, bus, truck, etc., which may have differing operating and data storage criteria; as well as the features accessible through the first programming level.

In the case of bus use, for example, the bus brake pedal is monitored for activity through vehicle input interface 68. When the bus is in normal operation and motion brake pedal usage will occur at an expected frequency. The expected frequency can be monitored such that the driver will not be required to give a sample during such normal operation. If the bus is stopped for a long period of time with the engine running, such as when the driver is having lunch, the system can detect the next time the brake pedal is used and require the driver to provide a breath sample. This prevents the embarrassing situation of requiring the driver to provide a breath sample while there are passengers aboard the bus. Another time the driver can be required to provide a breath sample is prior to starting the bus's engine. An override keyswitch can be connected to the interface 68 input to allow a supervisor to start the bus's engine without the requirement for a breath sample. After the bus's engine has been started in this manner and the override switch is returned to off, the next time the brake pedal is used the driver will be required to provide a breath sample. The override keyswitch can also allow the bus to be driven by a mechanic for maintenance purposes without the requirement for a breath sample if the keyswitch override is in the "on" position.

When the system is installed in a school bus a buzzer or other sounder can be installed at the front of the bus and connected to one of the relay outputs 72, and a pushbutton safety switch installed at the rear of the bus and connected to one of the interface 68 inputs. When the bus's engine is shut off the sounder will sound. The driver must then go to the rear of the bus to press the pushbutton to stop the sound and reset the system. The travel of the driver from front to rear of the bus allows inspection of the seats, and prevents children who may have fallen asleep from being left on the bus. The sounder can be interfaced with an override keyswitch to disable operation when appropriate.

The present invention provides for great flexibility in use, with simplified and economical production of a control module, as only one version of the board needs to be produced. The intended use; voluntary, mandate, bus, school bus, etc. is determined by a setting of the appropriate configuration through the RS-232 interface as described above. The configuration setting, a level 2 function, is intended to be set during production, and would not normally be available to field personnel. Connections to the vehicle are made through appropriate interface cables that connect to the input interface 68 and the relay outputs 72 by means of connectors on or associated with a printed circuit board on which the microprocessor and other components are mounted, as known in the art. Since different models and functionality may require connections and wires with different functions in the interface cables, it may be advantageous to provide contacts for wires for all configurations can be included in the connectors. During production only those wires needed for the intended end use can be included in the interface cables. This eliminates the need to stock a wide variety of boards, and also results in the ability to provide custom configurations using the same board. Functionality may be changed either by re-programming ROM 58 or by changing the ROM to one having the appropriate instruction set.

Another embodiment of the invention is a version particularly adapted for automobile use. This version uses two smaller control modules instead of one; the first, a Central Processor Unit (CPU), would incorporate the microprocessor 54, RAM 56, ROM 58, nonvolatile RAM 56 for storage of events and setup information, the A/D converter 62, the speech processor 64 and the RS-232 interface 76. The second module, the car control module (CCM) would incorporate the relays 72 necessary to control vehicle functions; the relay interface 70; the vehicle signal input interface circuitry 68; and the audio amplifier 66. The two modules would include connectors for connection of the sensor head 10 to the CPU, an interconnecting cable from the CPU to the CCM (CPU/CCM interconnect cable) and a connector to allow the CCM to be connected to various circuits in the vehicle (vehicle interface cable). This design can provide for an easier installation in cars with limited space under the dashboard, since the two modules do not have to be installed in the same location. All features of the CPU would be programmable through the RS-232 interface including, but not limited to, the selection of all languages for the voice messages, setpoint setting, limits for breath pressure and duration, the number of rolling retests and their duration, and the current date and time.

An enhancement that can be included in either version of the control module is the addition of a form of positive identification to deter circumvention of the system. The most common type of circumvention occurs when someone other than the driver provides a breath sample to start the vehicle. The driver then proceeds to drive, possibly with a breath alcohol limit over the setpoint. The enhancement comprises means to record a preferably digital picture of the user taken during the first breath sample when the vehicle is started. This picture serves to identify the "driver". Subsequent pictures would also be taken during rolling retests. If a retest result is satisfactory, the picture may or may not be saved. The pictures can be saved on a random basis to prevent the driver from knowing when a picture is to be saved while minimizing memory needed to save the images. If the rolling retest is failed, the picture of the first breath sample would be available, along with the picture of the failed test taker. With reference to FIG. 4, this enhancement can be implemented in the form of an infrared video camera 78 mounted facing the driver's position; an infrared light source 80; a video processor 82; and memory 84 in the form of a hard drive or solid state devices. The foregoing may all form an integrated system, provided by third-party suppliers, such as VerifEye Technologies of Ontario, Canada. The video processor may comprise a microprocessor 86; RAM 88; ROM 90; video interface 92, a memory interface 94; and an interface 96 to the microprocessor in the control module. The camera is connected to the video processor, while the external memory is connected to the processor as known in the art using a memory controller. As known in the art, the type of controller may be dependent on the type of memory used. The video processor 82 can be located in the control module or can be located in a separate case. Operating software, for processing and storing the picture data can be stored in the ROM as, while the video processor interfaces to the microprocessor in the control module, whereby camera operation is controlled. Any circumvention attempts would be recorded by the nonvolatile RAM in the control module. In addition, recognition/comparison software can be utilized to provide "on the fly" analysis of the photographs to immediately determine if the same individual appears in compared photographs. Appropriate outputs can be generated in the event a discrepancy is found.

Figure 5:
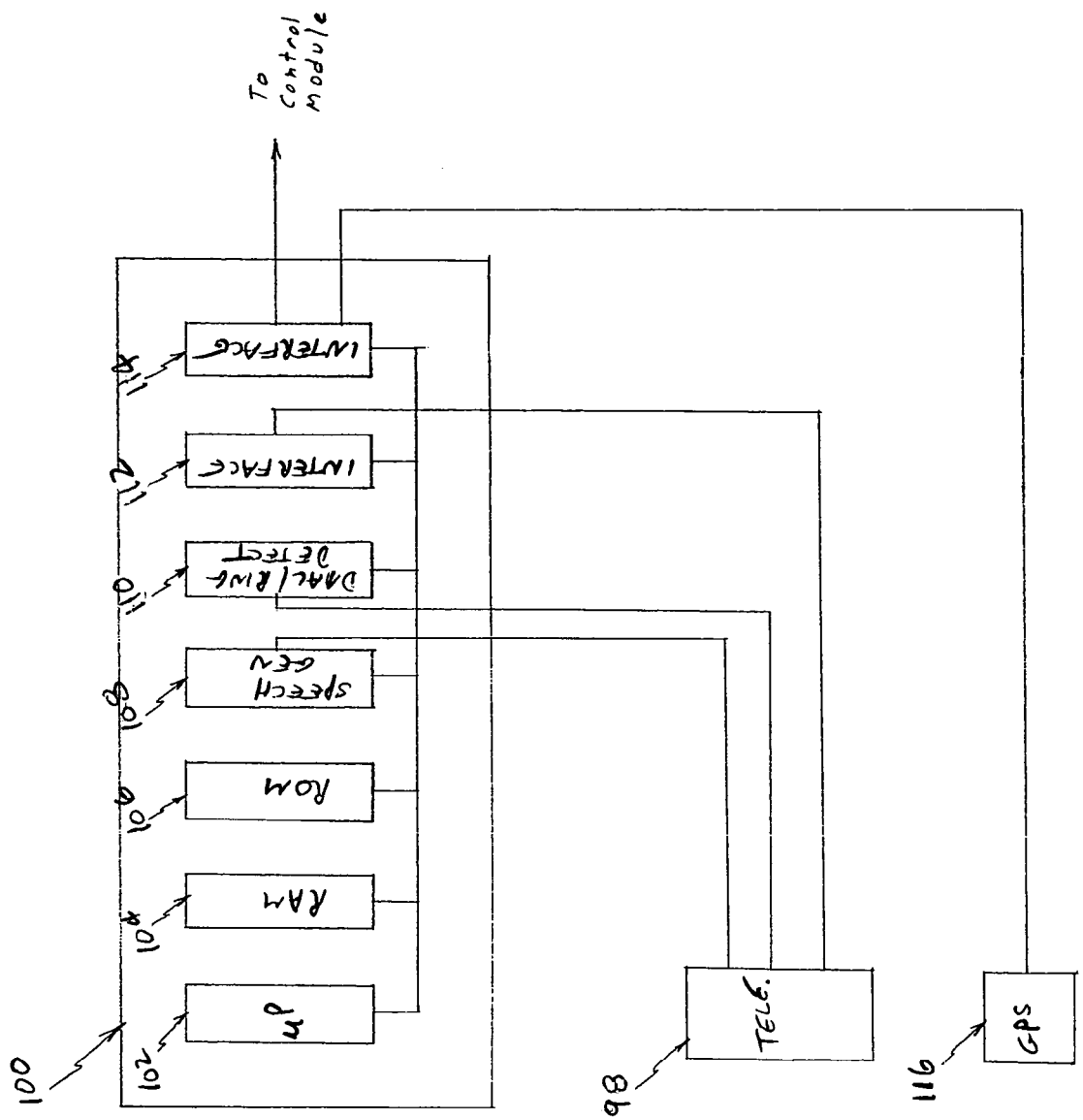
FIG. 5 is a block diagram of a cellular telephone interface for the invention.

In a further embodiment an interface to a cellular telephone or similar communication may be incorporated into the system. As shown in FIG. 5, the cellular telephone 98 is connected to an interface unit 100. If a startup test or rolling retest is failed the phone automatically dials a number stored in software. A recorded message transmitted by the telephone may state that a breath test had been failed, and provides information about the driver and the vehicle's make, model and license number. This information may also be sent in the form of encoded data. Alternatively, the telephone number of the cellular telephone may be used to identify the driver and/or vehicle. The vehicle's location can be determined through the cellular network or a GPS (Global Positioning System) receiver 116. The interface may consist of a microprocessor 102; RAM 104; ROM 106; a speech processor/generator 108; a dial tone and ring detector 110, an interface 112 to the telephone's keypad; and an interface 114 to the GPS unit and to the microprocessor in the control module, Software associated with the interface 112 turns the telephone on, obtains a dial tone, and dials a number stored in the software. The software then waits for a ring tone, repeating the entire process (wait for dial tone, dial and wait for ring tone) until the ring tone is detected. Once the ring tone is detected, the system awaits connection. This can be accomplished, for example, though a counter in the software counting, for example, ten rings. If the full number of rings is counted, signifying a failure of pick-up at the dialed number, the entire process (wait for dial tone, dial, wait for ring tone, count number of rings) would then be repeated. This would continue until the ring tone count ended before ten rings, indicating that the call has been answered. A recorded message from speech generator 108 would then be played or encoded data transmitted. The software would keep the phone active until the connection at the other end was broken. The stored number could be 911 or that of a central dispatch location. The message played or the data sent can be dependent on what event had occurred, i.e., start up test failed, rolling retest failed, etc. Those skilled in the art can readily recognize that in place of the cellular telephone other transmitters or transmitter/receiver combinations can be employed, to access a satellite link for example, which could communicate with a central dispatch location.

The cellular telephone or satellite link could also be used to transmit (download) data that is stored in the control module's nonvolatile RAM upon receipt of a command from a central dispatch location. This function can be used to satisfy requirements for periodic downloads for mandatory installed units without requiring the driver to return to a download center. Such a link can also provide the ability to monitor and repot vehicle usage and events at any time.

We claim:

1. An ignition interlock device, comprising a sensor head coupled to a control module having a microprocessor, the sensor head including a breath sample passageway and breath pressure and breath alcohol-responsive sensors for generating a respective output as a continuous function of the parameter sensed coupled to the passageway, and an audible output generator, said control module including means for control of vehicle operation as a function of signal outputs generated by the sensor head, and a switch for alternatively selectively passing one of the outputs of the breath pressure and the alcohol-responsive sensors to the control module.

2. The device of claim 1 wherein the switch is located in the sensor head and is controlled by the microprocessor.

3. An ignition interlock device, comprising a sensor head coupled to a control module having a microprocessor, the sensor head including a breath sample passageway and breath pressure and breath alcohol-responsive sensors for generating a respective output as a function of the parameter sensed coupled to the passageway and an audible output generator, said control module including means for control of vehicle operation as a function of signal output generated by the sensor head, and wireless means for real time reporting test results to a remote location during vehicle travel without otherwise affecting the operation of the vehicle.

4. The device of claim 3 further including means for monitoring vehicle brake operations during normal operation of the vehicle as an input to the control module.

5. The device of claim 3, wherein the wireless means further comprises means for transmitting vehicle position data to the remote location.

* * * * *